United States Patent
Summer et al.

(10) Patent No.: US 8,241,498 B2
(45) Date of Patent: *Aug. 14, 2012

(54) PROCESS FOR REMEDIATING BIOFOULING IN WATER SYSTEMS WITH VIRULENT BACTERIOPHAGE

(75) Inventors: Elizabeth Summer, Caldwell, TX (US); Neil S. Summer, Caldwell, TX (US)

(73) Assignee: Phage Biocontrol Research, LLC, College Station, TX (US)

( * ) Notice: Subject to any disclaimer, the term of this patent is extended or adjusted under 35 U.S.C. 154(b) by 242 days.

This patent is subject to a terminal disclaimer.

(21) Appl. No.: 12/731,121

(22) Filed: Mar. 24, 2010

(65) Prior Publication Data

US 2010/0243563 A1     Sep. 30, 2010

Related U.S. Application Data

(60) Provisional application No. 61/164,413, filed on Mar. 28, 2009.

(51) Int. Cl.
*C02F 3/00* (2006.01)
*C12M 1/34* (2006.01)

(52) U.S. Cl. .................................... 210/606; 435/287.1

(58) Field of Classification Search .................. None
See application file for complete search history.

(56) References Cited

U.S. PATENT DOCUMENTS

| | | | |
|---|---|---|---|
| 4,778,653 A | 10/1988 | Kamimura et al. | |
| 6,699,701 B1 | 3/2004 | Sulaknalidze et al. | |
| 2008/0213752 A1* | 9/2008 | Stave et al. | 435/5 |
| 2009/0180992 A1 | 7/2009 | Summer et al. | |

OTHER PUBLICATIONS

Sakaguchi, et al (Control of Microbiofouling Using Bacteriophage 2. Detection of Phages and Fundamental Study of Their Lytic Effect on Fouling Bacteria (Abstract Only), De.
Leee & Newman; Molecular analysis of a mixed-soecies biofilm on carbon steel; Abstracts of General Meeting og the American Society for Microbioligy, vol. 103, p. Q-156, 2003.
Sakaguchi, et al; Control of Micrio Fouling Usinf Bacteriophage 2. Detection of Phages and Fundamental Stuf dy of Their Effect on Fouling Bacteria; Denryoku Chuo Kenkyusho1989.
Sakaguchi, et al (Control of Microbiofouling Using Bacteriophage 2. Detection of Phages and Fundamental Study of Their Lytic Effect on Fouling Bacteria (Abstract Only), De, 1989.
Lee, et al (Molecular analysis of a mixed-species biofilm on carbon steel. Abstracts of the General Meeting of the Americam Society for Microbiology. 2003; vol. 103:Q-156).
Zacheus et al, Soft Deposits, The Key Site for Microbial Groth in Drinking Water Distribution Networks; Wat. Res. Vi ol. 35, No. 7, pp. 1757-1765,2001.

* cited by examiner

*Primary Examiner* — Shanon A Foley
(74) *Attorney, Agent, or Firm* — Douglas Baldwin

(57) ABSTRACT

Bacterial contamination of industrial water systems lead to biofouling by biofilms and corrosion from bacterial induced corrosion. This invention provides a method for control of fouling and contamination of industrial water systems caused by bacteria. Prevention or reduction of process interruptions and general contamination, fouling and corrosion is achieved by the destruction of targeted problematic bacteria with naturally occurring, non-engineered bacteriophage virulent for targeted bacteria. The invention also provides for in-situ confirmation of the proper identification of target bacteria and a mobile laboratory adapted to implement the method.

18 Claims, No Drawings

PROCESS FOR REMEDIATING BIOFOULING IN WATER SYSTEMS WITH VIRULENT BACTERIOPHAGE

RELATIONSHIP TO OTHER APPLICATIONS

This application claims benefit of Application Ser. No. 61/164,413 filed Mar. 28, 2009.

FIELD OF THE INVENTION

This invention relates to control of fouling and contamination of industrial water systems caused by bacteria. More specifically, it relates to prevention or reduction of process interruptions and general contamination, fouling and corrosion by the destruction of targeted problematic bacteria with naturally occurring, non-engineered bacteriophage virulent for targeted bacteria.

BACKGROUND

The nearly universal presence of bacteria are the cause of numerous problems, process interruptions including bulk foaming, biofouling from the accumulation of biofilms and microbial influenced corrosion (MIC) of industrial infrastructure.

It has been reported that the yearly cost of corrosion to sewage and drinking water is $36 billion, and in additional $17.6 billion to general production and manufacturing industries. These annual costs of bio-deterioration are huge, resulting in, e. g, failure of metallic heat exchanger equipment, corroded or blocked concrete sewer pipe, biologically attacked textiles or decaying pieces of cultural property. It has been also been reported that MIC caused damage of approximately US $ 55 millions in stainless steel heat exchangers alone within an 8 year period (Brennenstuhl et al., 1991). MIC is the most important factor determining the lifetime of water heater systems (Bresle, 1981).

Open flowing water will contain predominantly aerobic bacteria whereas biofilms will harbor both aerobic and anaerobic bacteria. In addition there are medically harmful "pathogenic bacteria" that exist alongside the bacteria that result in fouling and corrosion of equipment as well as beneficial bacteria which are utilized to break down biomass and other needed tasks. The diversity of the bacteria strains present significance challenge to control. For adequate control it is desirable to kill both the aerobic bacteria in the flowing water and the anaerobic bacteria in the biofilms and to retain advantageous bacteria. These desirable bacteria are often purposely added to sewage and waste streams, and toxic waste dumps to facilitate processing and clean-up.

Cooling water systems are particularly plagued with biofouling and corrosion. These systems provide an ideal environment for bacteria growth and nurture. Cascading water in cooling towers picks up airborne bacteria as well as bacteria from the surface of the equipment in which it is used. As a result cooling system water contains a large variety of bacteria including sulfur-reducing bacteria (SRB), which are a principle source of MIC corrosion, as well as other biofilm forming bacteria. Since the water from cooling systems is used in heat exchange and other equipment they often become fouled from biofilm generated in the cooling water system.

Equipment in paper production is also especially subject to biofouling. In papermaking, water is used not only for cooling but also as process water. Thus, anything in the process water ends up in the paper. If strong biocides are used in the process it leads to unacceptable levels of toxic chemicals in the paper itself.

While cooling water system and paper making water systems represent extreme cases of bacterial contamination, other water systems have similar problems. For example, bacterial contamination of swimming pools must be controlled, especially in public pools. Fire extinguisher water systems, while closed, often utilize water that has been in the open, or otherwise have bacterial problems similar to open industrial water systems, are also susceptible to biofouling and corrosion. Tom Hartel, President of Valley Fire Protection Systems, LLC, located in Batavia, Ill. recently has this to say about MIC in fire extinguisher systems:

"You work diligently to protect your building from fire. You install a quality sprinkler system with state-of-the art piping and heads. You conduct regular inspections. Then a fire breaks out and your system fails."

In 1998, a nursing home in Iowa experienced a situation where the sprinkler heads failed to release water during a fire, due to their being totally plugged with thick rust deposits as a result of MIC. Also, a very large, federal government research facility in Illinois has a well documented case of MIC pinhole leaks in one of the cooling water systems, and the National Fire Sprinkler Association has documented more than two dozen cases of MIC in their technical report dated June 1998.

Such reports of MIC in fire protection systems have grown significantly over the past decade. Newer systems, which employ a broader variety of piping materials, can be the most vulnerable. The problem is exacerbated by MIC's aggressiveness, which can penetrate pipes in just a few months. Once the MIC bacteria attaches to the metallic components, it grows rapidly and, to the untrained eye, spreads undetected. The National Fire Protection Association (NFPA), together with water, bacteria, and metallurgical experts are aware of the surge in recent MIC related activity, and are working to develop effective management and inspection guidelines, standards, and solutions.

Various industries, such as power utilities, have established extensive water treatment programs and procedures to tackle bacterial problems.

MIC affects a variety of materials (steel, stainless steel, aluminum, copper and cement), systems (wet and dry), and in all geographical areas from the arctic to the tropics. Chemical biocides are, at best, only marginally effective in controlling bacteria that result in fouling and corrosion. Moreover, biocides are expensive, dangerous, and often toxic to humans, animals and the environment. In particular, chemical biocides are largely ineffectual against sessile bacteria protected in complex biofilm communities, and it is exactly these chemically resistant biofilm communities that are the source of most biofouling and bio-corrosion. Oxidizing biocides that are somewhat effective against some strains of bacteria in an aqueous environment are frequently ineffective against SBR bacteria.

The definition of a perfect biocide may be found in an early NACE (National association of Corrosion Engineers) Biocide handbook:

"The ideal biocide will be effective against species that cause biofouling and bio-corrosion without interfering with the development of other species. Moreover it should be safe and easy to handle, in order to maintain the health of those people that handle it. It should be biodegradable and the intermediate products of its biodegradation should be less toxic than the original." The "shotgun" or broad spectrum approach of chemical biocides has proven over the years to be ineffectual and result in resistant bacteria. What is needed is the perfect biocide. The present invention, utilizing an effective, specific, cheap, safe to handle, natural and environmentally benign bacteriophage to control befouling and corrosion is such a biocide.

SUMMARY OF THE INVENTION

This invention is, in broad aspect, a method of remediation of biofouling and bio-corrosion in industrial water systems comprising;
identifying a target bacteria strain in a water system;
locating and enriching a phage or phages virulent for said bacteria strain, and
subjecting said water system to an effective amount of said phage or phages to effect a reduction in the number of the bacteria.

The invention is preferably utilized in water systems, including but not limited to industrial cooling water, sewage and drinking water systems and all forms of industrial process water e.g. paper making water, swimming pool water and fire extinguisher system water.

A generic phage-based bioremediation system includes at least one infective phage wherein the phage reduces bacterial contamination within a water system. A phage-based anti-corrosion system also includes an infective phage panel wherein the panel reduces selected bacterial populations capable of generating corrosive metabolites and/or developing a biofilm.

In one embodiment the invention is also a mobile laboratory having means designed for identifying a target bacteria strain in an open water system and enriching a phage virulent for said bacteria strain comprising; a source of electric power; an enclosable working space that can be maintained clean and sterile; a side loop or container for culturing bacteria that is also equipped with a transfer means and connection means to connect a container vessel to a target water source; a centrifuge and/or filter for enriching the bacteria and/or phage; testing equipment for identification of bacteria and for phage.

DETAILED DESCRIPTION

Bacteriophage or phage is the perfect biocide: targeted, benign to all other life forms, easily disposable, and cheaper than chemical biocides. Phages are natural, found in all environments where bacteria are present, and are water-borne predators of bacteria. In a typical phage cycle, a single phage recognizes and injects its DNA into a specific bacterium. Inside the bacteria, the phage replicates itself and then releases its progeny by bursting out of the bacteria. In less than an hour, the host is dead and there can be as many as 300 further predatory nanoparticles to seek out further problem causing bacteria. A solution of phage virulent for target bacterial or a mixture or panel of phage, or a phage "multi-panel", can be injected into a bacteria containing open water system to destroy harmful bacteria, eliminate fouling biofilm and remediate bacteria influenced corrosion. This invention sharply reduces the use of toxic and environmentally unsound biocides.

As used herein the following definitions apply: A phage cocktail includes multiple, receptor independent phages for each target bacterial host. This is different from a phage panel, which is a collection of phages chosen to cover as wide a host range as possible. For the purposes of this invention the phage treatment of waters will consist of a panel of phage cocktails, that is, there will generally be at least two virulent phages for each target bacterial and phage cocktails for each of several target SRB bacteria. Since some SRB phages are known to be polyvalent—effective against more than one strain of SRB—there may not need be a separate cocktail for every strain of target bacteria. This panel of cocktails is designated herein as phage "multi-panel".

Unlike medical treatment therapies or agricultural use of phage control of bacteria, industrial open water systems have a variable and often unpredictable population of bacteria. Therefore, it is desirable that the bacterial population for each water treatment application be first identified so that an effective phage panel can also be identified, produced and applied. This requires a multi-step process consisting of the following:

First, samples of the target water source are collected and the bacteria assayed. Bacteria assay is accomplished by any of several means known to those in the art. For example, the identity of bacteria may be determined by denaturing gradient gel electrophoresis (DGGE) or TGGE (temperature gradient gel electrophoresis) DGGE is a relatively fast and cost effective to determine the bacteria community. Identified target bacteria strains are individually cultured for selection of an effective killer phage. An effective bacteriophage will generally not be one that naturally co-exists with the bacteria—coexisting phage are usually temperate (not virulent). Often, however virulent phage specific to the target bacteria will exist in the surrounding area or vicinity of the of the target bacteria.

Next, effective virulent phages are identified. To determine an effective phage, if one is not already known, samples are taken from the bacteria containing water or the surrounding areas, e. g. from the soil, equipment or other water sources such as streams or ditches. The bacteria containing water often contain the virulent phage(s) but in concentration too low to effectively infect and destroy its matching bacteria. The identified phage(s) gives an array of potential virulent phages. Individual phage species from each are isolated and enriched. Each phage is then tested on the target bacteria to determine if it is capable of killing the bacteria.

In one embodiment, when suitable phages are identified each strain is mixed with its targeted bacteria to grow a sufficient quantity for in-situ trial in the target water environment. It is preferred that for open water systems the testing will be made on a side-stream or other aliquot of the water to be treated. Testing of biofilms can be made on a suitable aliquot of the offending film. Each phage may be individually tried for effectiveness. In another embodiment mixtures of three or more phages in a phage "multi-panel" determined to be effective will be prepared for use on waters with multiple target bacteria. If the test is successful, that is, if the target bacteria population is reduced by contact with the phage, a treating phage mixture (cocktail) is prepared from the identified phage strains. For example if three phages are chosen to counter five (5) problem bacteria or strains of the same bacteria, said cocktail could contain 15 phages at their appropriate "Minimum Inhibitory Concentrations."

Prepared phage strains may be freeze dried or encapsulated for storage and later use.

The process of the invention may be summarized by the following steps:
1. Identifying target bacteria.
2. Culturing dominant virulent bacteria strains.
3. Identifying virulent phage for the offending bacteria—e.g. matching virulent phage with its associated bacteria strain.
4. Isolating and enriching phage samples for testing.
5. In-situ test of identified killer phage strains.
6. Preparing suitable quantity of identified phages (cocktail) to treat the target water system.

7. Treating the target water source with an effective amount of phage cocktail.

These steps are more completely explained below:

1. Identifying Target Bacteria:

Target bacteria are identified by sampling from the water and/or biofilm showing bio-corrosion and fouling. From samples the target bacteria can isolated and characterized, to some extent based on what is generally already known about the causes of corrosion and fouling.

Sulfate-reducing bacteria (SRB) one of the causes of microbially influence corrosion (MIC) and filamentous bacteria such as *Gordonia* and entrained species cause bulk foaming and process upsets). The SRB reduce sulfates to sulfides and produce hydrogen sulfide and sulfuric acid. Hydrogen sulfide also reacts with iron to form the characteristic black precipitate of iron sulfide. The term "SRB" is a phenotypic classification and several distinct lineages of bacteria are included under this umbrella term. The most widespread are members of the delta subgroup of the Proteobacteria, including Desulfobacterales, Desulfovibrionales, and Syntrophobacterales. Bacteria selected for phage treatment may include all members of the SRB including, including without limitation, isolates of *Desulfovibrio, Desulfotomaculum, Desulfobacter*, and *Desulfuromonas*. Specific members include any isolates similar to or identical to *Desulfovibrio vulgaris* and *D. desulfuricans*. These bacteria are also known to mediate corrosion through interactions with the hydrogen film on water-exposed iron. Bacteria selected for phage treatment also includes those that produce acidic metabolites. This specifically includes sulfur-oxidizing bacteria capable of generating sulfuric acid. This includes, without limitation, sulfur bacteria such as *Thiobacilli*, including *T. thiooxidans* and *T. denitrificans*.

Bacterial populations and isolates targeted for phage treatment further includes corrosion associated iron-oxidizing bacteria and also bacteria in the family Archaea. Also included are isolates of the Caulobacteriaceae including members of the genus *Gallionella* and *Siderophacus*.

Still further bacterial populations may work synergistically with the problem bacteria. These include members of microbial consortia exhibiting biofilm formation activity. Such biofilms can provide the microenvironment required for the growth of the problem bacteria. As such, the target of phage treatment can include not just corrosive metabolite producing bacteria but also any bacteria involved in forming the microenvironment required to upset industrial processes and cause fouling and corrosion. Additionally, biofilm producing bacteria involved in the biofouling process are included in the category of targets for phage remediation. Biofilm forming genera of bacteria include *Pseudomonas* or *Vibrio* species isolated in affected containment systems. Bulk foaming is also a form of biofilm that interrupts settling in the process of sewage treatment. Bacterial populations responsible for biofilm blockage may also be selected for phage treatment. All bacteria that are to be the targeted for phage treatment are part of the selected bacterial subpopulation.

2. Culturing Target Bacterial Strains:

The target bacteria are cultured by means well known in microbiology. Any means of culturing bacteria that promotes growth of the bacteria population are suitable. For example, as used in the Example below, liquid cultures of *D. vulgaris* were grown in ATCC medium 1249 Modified Baar's medium for sulfate reducers. Plate cultures of *D. vulgaris* were grown on ATCC medium: 42 *Desulfovibrio* medium. Cultures were grown at either 22° C. or 30° C. in anaerobic GasPak jars (VWR). *D vulgaris* growth forms a characteristic black precipitate in media containing ferrous ammonium sulfate, an indicator of sulfate reduction.

Sufficient bacteria can be grown and enriched in relatively small container. Therefore, it is preferred that the initial culturing of bacteria be conducted on site or in-situ. Larger quantities, as are needed for large scale production of phage, are preferably grown in a centralized location having the equipment and resources needed.

Some offending target bacteria may not be culturable. To test and proliferate the phage necessary for treatment, an on-site side loop mobile facility is used in one embodiment. This facility may a mobile, for example a building mounted on a truck, trailer or skids. In this facility the actual product will be the growth media with testing done in flow loops filled with the actual contaminated water.

3. Identifying Virulent Phage for Target Bacteria:

The geographic distribution of industrial bacterial contaminations is world-wide and transverses many geographic and geological boundaries. Similarly, the sources of phages for controlling bacterial infestations include any site where bacteria are found and thus transverses many geographic and geological boundaries. While existing phage stocks will be screened for activity on contaminating bacteria, new phages will also be isolated from the same site or location where the bacteria pose a problem.

As the natural predators of bacteria, populations of bacterial phage will be most abundant near abundant sources of their prey. Therefore, the logistics of identifying phage specific for any bacterial population is to first identify an environmental site where that bacterial type is abundant. This means that there is not one environment that will serve as a source of phage for all target microbes. Instead, the exact environmental sample will vary from host strain to host strain. However, there are general guidelines for identifying the environmental sample most likely to yield desired phages. An ideal sample is a marine or freshwater sediment from an environment favorable for the growth of the host bacteria. Specific physiochemical properties of the sediments are important. While the exact parameters will vary from host to host, variables to consider include salinity, temperature, pH, nitrogen or eutrophication, oxygen, and specific organic compounds. An example, which is not intended to be a guideline for all protocols, would be the identification of phage active against a sulfate reducing bacterium (SRB) such as *Desulfovibrio*. Sediments enriched in SRB are characterized by a black anoxic layer and the production of odiferous volatiles such as hydrogen sulfide. These sediments are common in areas experiencing eutrophication in concert with the resulting oxygen depletion. Therefore, a sample likely to possess SRB specific phages would be a black, hydrogen sulfide producing sediment collected from organic compound rich waters.

The choice of sample site for phage isolation is customized to a specific host. Phage isolation sites may include any body of water (natural or man-made), sediments, or soil samples. Phage isolation sites may also include man-made structures such as the target water source, containment or settling tanks, creeks and ditches. Within the man made structures, the sludge-like deposits composes of organic and inorganic sediments that have settled at the bottom of the structures are often the optimal sampling site for isolation. Phages for any given host can be found at the same conditions relative to salinities, temperatures, pH, pressure, nitrogen concentrations, oxygen levels that are favorable to the growth of the host bacteria. Bacteria vary greatly with regard to carbon source utilization, similarly phages that infect these bacteria can be found in these environments regardless of carbon source being utilized by the bacteria. Similarly, bacteria vary greatly with regard to tolerance and utilization of industrial waste materials such as metals, heavy metals, radioactivity, and toxic chemical wastes including pesticides, antibiotics, and chlorinated hydrocarbons.

As an alternative to identifying samples based on physiochemical properties, molecular tools are used to identify sediments possessing wild populations of bacteria similar to the target bacteria. These methods typically require some level of purification of DNA from the environmental sample followed by the detection of marker DNA sequences. The most straightforward of these are polymerase chain reaction (PCR) based technologies that target 16 s rDNA sequences. These can be analyzed by methods such as denaturing gradient gel electrophoreses (DGGE or TGGE) or by DNA sequencing.

4. Isolation of Novel Phages Active Against Target Bacteria:

It is necessary to match a collected phage to a target strain of bacteria; matching in the sense of obtaining a phage sample that is specifically virulent (killer) for the collected bacteria strain. Matching is accomplished by identifying the bacteria strain and empirically applying a phage sample until a kill of the bacteria is obtained. It may also be accomplished without ever identifying the bacteria strain by empirically finding a matching killer phage from collected or stored phage samples. These empirical methods are more research intensive than specifically identifying the bacteria and/or the killer phage, but are equally effective for the purpose of this invention.

Using criteria discusses above with respect to the individual characteristics of the target bacteria, an appropriate environmental site will be identified from which phages can be isolated. The primary methodology used to isolate these phages is an enrichment method. Sediment, sludge, or soil samples from the environmental or industrial site will be mixed with a solution containing salts and peptides. The exact composition of this solution can vary but in general will approach the same composition as Lysogeny Broth (commonly referred to as LB media: per Liter—10 g tryptone, 5 g yeast extract, 10 g NaCl). The ratio of sample to LB will vary, with the goal of producing a thick turbid sludge. This is shaken for several hours and a sterile rinsate is produced from it by sequential centrifugations and filtrations to remove solid material greater than 0.2 microns. This is termed a "rinsate" and the rinsate is then supplemented with concentrated fresh bacterial media (which will vary depending on the exact bacterial host being grown). A small amount of the host is then added to the rinsate/media mix and allowed to incubate for one to several days depending on the growth rate of the host. Incubation conditions including shaking, media temperature and oxygen levels will be those that promote growth of that particular host. After incubation, chloroform will be added to 0.01% and the solution will be sterilized by sequential centrifugation and filtration to remove intact bacterial cells. This solution is termed an "enrichment". Phages in the enrichment are assayed for by several different methods including the plaque assay, liquid culture lysis, or visualization by electron microscopy.

The final product is an aqueous solution containing the phage particles in a weak phosphate buffer with minimal bacterial cellular debris.

5. In-Situ Test of Identified Killer Phage Strains:

Matching of the identified phage and target bacteria or biofilm in isolation is critical to the success of the process of this invention and must be validated in "real life" conditions of the environment in which it is to be used. Thus the matched phages are tested in the water conditions that exist. This is suitably done in a side-stream or aliquot of the water system to be treated. A suitable means for this tests, for example in a cooling water system, is to pump a stream of the water source into a suitably sized container or side loop for sufficient time to allow it to come to equilibrium with the water source. It is important to note that the concentration of both target bacteria and phages must be sufficiently high to allow initiation of infection and to allow the infection and lysis to be accomplished in a reasonable time, for example in less than about five hours and preferably less than two hours. In order to accomplish this, the concentration of target bacteria must be above about $1 \times 10^5$ cfu/ml and the concentration of phage(s) must be above about $1 \times 10^5$ u/ml.

The identified phage or phages are introduced into the stream (either batch wise or in continuous flow) and tests are made to determine if the population of target bacteria are reduced.

In another embodiment this step is accomplished in a mobile testing laboratory as described below.

6. Preparing Suitable Quantity of Identified Phages (Cocktail) to Treat the Target Water System:

The treatment "cocktail" or "panel" consist of a mixture of virulent phages that have been found to "match" the target bacteria and biofilm. Sufficient phages must be manufactured to provide an effective amount to significantly reduce the target bacteria population.

For this, phages exhibiting bacteriolytic activity against corrosion associated or causing bacteria will be selected. Phage panels may include pre-existing phage isolates as well as the de novo isolation of novel phages from samples taken at the water site. Thus, in one embodiment, the step of producing the infective (virulent) phage panel further may include screening and isolating naturally occurring phages active against the selected bacterial population. In another embodiment, it may be unnecessary to screen for phages where the suspect bacterial populations are already known or suspected. Phages may be isolated by a number of methods including enrichment methods or any technique involving the concentration of phages from environmental or industrial samples followed by screening the concentrate for activity against specific host targets. Additionally, new methods for isolating phages are likely to be developed and any phages isolated by these methods are also deemed covered by the claims of this invention. Given the high genetic diversity of phages, these naturally occurring phages will include those with novel genomic sequence as well as those with some percent of similarity to phages known to infect other bacterial clades. Most of these new phages are expected to be members of the taxonomic group Caudovirales, also generally referred to as the tailed phage. The use of phages in an infected cocktail is dependent on the phages bacteriolytic activity. Bacteria targeted by treatment with phage or phage panels includes any isolate present in the target water system.

Phages can be optimized for effectiveness by selection for naturally occurring variants, by mutagenesis and selection for desired traits, or by genetic engineering. Traits that might be optimized or altered include, but not limited to, traits involved in host range determination, growth characteristics, improving phage production, or improving traits important for the phage delivery processes. Thus, in another aspect, the step of producing the infective phage panel includes creating engineered phages against the selected bacterial population. This will include phages created for having a broad host range. This may be the product of directed genetic engineering, for example.

Collectively, the phages pooled together are referred to herein as the infective phage panel. Initial treatment of a target water system with the infective phage panel is ideally followed up by monitoring of the contained system to reveal the effects on the selected bacterial subpopulation. Over longer periods of time it may be necessary to alter the phage panel to confront bacteria that have developed resistance mechanisms to the infective phage panel. Additionally, new bacterial species may begin to thrive in the absence of the initial selected bacterial subpopulation. Thus, the need may arise to alter the infective phage panel over time. New infective phage panels may be created in response to either resistant strains or new bacterial populations causing biofilm fouling or bio-corrosion. The effectiveness of the infective phage panel is, in one embodiment, monitored by evaluating changes in phage and bacterial host populations within the system. One can either determine the presence of such bacterial populations directly, or simply monitor the formation of new biofilms and the reoccurrence bio-corrosion events.

Large Scale Phage Production

Phages are produced, in one embodiment, using a standard liquid lysate method. It should be noted that industrial scale phage production has been achieved inadvertently by the dairy industry and historically by the acetone/butanol fermentation industry which demonstrates the feasibility of aerobic and anaerobic phage production on this scale.

1. Prepare an exponentially (=OD600~0.3) growing stock of the target host in the volume of liquid corresponding to the desired final lysate volume. This is done by inoculating the media from a stationary stage liquid culture to a very low (OD600~0.01) and monitoring growth specrophotometrically until the desired OD is reached.
2. Inoculate this culture with phage to a moi (multiplicity of infection=ratio of phage particles to individual host cells) of 0.1 to 0.001.
3. The culture is then incubated until lysis is observed; typically over night but can take several days depending on the host growth rate. At this point the lysate is ready for purification of the phage particles away from both bacterial cell debris and the components of the culture media. This is accomplished first by vacuum filtration through a filter series with the final pore size being 0.2 m. Finally, tangential flow filtration will be used to replace components of the media with 10 mM phosphate buffer and, if necessary, to concentrate the phage.

Since phage are notoriously hardy, they may be concentrated, freeze dried and stored for long periods of time without lose of effectiveness. This allows phage panels (cocktails) to be shipped to remote locations for use. It allows the manufacture to be made at optimized central locations. While it is desirable the steps 1-6 be made "on location" it is generally preferred that the manufacture of the large scale phage cocktail be centralized in locations where the necessary equipment and resources are readily available.

7. Treating the Target Water Source with an Effective Amount of Phage Cocktail:

The infective phage panel is delivered by mixing an effective amount of phage panel into the target water system. For example, in a cooling water system an effective amount of phage panel in aqueous solution is poured into the circulating water or may be metered into the water over a period of time.

The rate at which phage infect and lyse target bacteria is highly dependent upon the concentration of phage and target bacteria. By slowly seeping the phage multi-panel into the water the phages forms a pocket of high concentration surrounded by concentrated bacteria. As the phages infect and lyse target bacteria the number of phage multiply exponentially so that as the phage diffuse through the water in a kind of wave of concentrated phage attack the surrounding bacteria. If on the other hand, the phage multi-panel is rapidly and thoroughly mixed with the water in large volume, the concentration is greatly reduced and the infection of bacterial slowed to unacceptable levels. This can be accomplished by adding phage(s) solution under the surface of the water slowly in discrete locations—such as can be accomplished with a soaking hose or similar injection means.

Simply adding the phage(s) or phage multi-panel to the water will be effective for bacteria in the water but there may be a need for more direct application for biofilm. While the phage produce enzymes (as, for example those used for rupture of the bacterial cell walls) that will penetrate the coating on the biofilm it may be desirable to also use a dispersant to help to break up the film in conjunction with the phage panel.

In one embodiment the biofilm is treated with an effective amount of dispersant to break up some of the biofilm to allow the phage(s) in the water to infect the bacteria so released from the film. In another embodiment phage(s) or phage multi-panel together with an effective biofilm dispersant is sprayed or otherwise suitably applied to the biofilm to be removed. An effective amount is that amount that will produce a measurable change in the desired direction.

The literature is replete with suitable dispersant for industrial biofilm. See, for example, US patent applications Serial Nos. 20080274929 that discloses the use of polyethyleneamine as a suitable dispersant and 20090318303 that discloses use of a group II capsular polysaccride and U.S. Pat. No. 6,080,323 that discloses the use of alkyl polyglycoside. Many more suitable dispersant and surfactants are commercially available.

The infective phage panel may also be delivered via a medium that coats at least a portion of any element of the target system. For example, the infective phage panel may be incorporated into a paint or coating to "inoculate" the walls or other locations that are subject to biofilm fouling (and consequence corrosion).

A generic phage-based bioremediation system includes at least one infective phage wherein the phage reduces bacterial contamination within a water system. A phage-based anticorrosion system also includes an infective phage panel wherein the panel reduces selected bacterial populations capable of generating corrosive metabolites and/or developing a biofilm.

In another embodiment this invention is a mobile laboratory designed for carrying out steps 1-5 described above. The laboratory is mobile—housed preferably in a vehicle or trailer which will contain essential equipment and working space. It comprises: a source of electric power (i.e. generator or means to connect to power or solar power system or any combination); a working space that can be maintained clean and sterile; a flow loop and series of test flow loops or containers for culturing bacteria that is also equipped with a pumping means and connection means to connect the flow loop to the target water source; a centrifuge for enriching the bacteria and/or phage; testing equipment for identification of bacteria and for phage (such as described in the example below).

The laboratory may also optionally contain a tangential flow filter for the concentration of bacterial and/or phage solutions.

The laboratory will also contain means for sterilization of the loop equipment before and after use. Sterilization before use will eliminate false results from preexisting bacteria and/or phages and sterilization after use will eliminate any residual bacteria or phages that may be of concern. Suitable sterilization means include bleach, hypochlorite, ultraviolet light, ozone and the like.

ILLUSTRATIVE EXAMPLE

The following example illustrates the effective steps of the present process and demonstrates its viability.

Experimental Procedure

Bacterial Culture: The host for a phage isolation study was the ATCC type strain, *Desulfovibrio vulgaris* subsp. *vulgaris* ATCC 29579. This strain is most commonly known as *Desulfovibrio vulgaris* Hildenborough and has been the subject of much corrosion based research. The genomic analysis of this strain has also been performed Liquid cultures of *D. vulgaris* were grown in ATCC medium 1249 Modified Baar's medium for sulfate reducers. Plate cultures of *D. vulgaris* were grown on ATCC medium: 42 *Desulfovibrio* medium. Cultures were grown at either 22° C. or 30° C. in anaerobic GasPak jars (VWR). *D vulgaris* growth forms a characteristic black precipitate in media containing ferrous ammonium sulfate, an indicator of sulfate reduction.

Phage isolation: Phage isolation was performed using an enrichment procedure. Black mud samples were taken from ditches in the area around Freeport, Tex. 50 g of mud (wet) was mixed with 50 ml of ATCC medium 1249 in 50 ml screw cap tubes. Samples were shaken at room temperature overnight. Chloroform was added to 0.1% v/v and the sample was shaken for an additional 30 minutes. Solids were pelleted by centrifugation (4,000 g, 20 minutes). The supernatant was filtered sequentially through 0.8 µm and 0.22 m filters. 25 mls of this bacteria-free rinsate was mixed with 25 ml of fresh media and inoculated with 500 µL of a logarithmically growing liquid culture of *D. vulgaris* Hildenborough. This was incubated overnight incubation at room temperature followed by the addition of 500 µl of chloroform, pelleting for 9,000 g for 10 min and sequential filtration through 0.8 µm and 0.22 µm filters, forming enrichment 1 (E1). Phages in E1 were amplified in a liquid lysate by inoculating 50 ml of fresh media, with 50 µl of E1, and 500 µl of the host. The culture was incubated overnight and phage were purified away from bacterial cells by chloroform treatment, centrifugation, and filtration using the same method that enrichment 1 was purified. This sample was called enrichment 2 (E2).

Phage Plating and EM Imaging: The presence of phage in E1 and E2 was determined using a spot assay. Agar plates were flooded with 500 l of *D. vulgaris* Hildenborough and allowed to dry for 10 minutes. Excess liquid was removed by pipetting 5 l of E1 and E2, along with a media control, was spotted onto the surface followed by anaerobic incubation. Phages present in E2 were imaged by TEM by spotting onto 400 mesh carbon-coated copper grids and negatively stained with 2% (w/v) uranyl acetate. The samples were visualized with a JEOL 1200 EX at 25,000×mag, 100 kV, and scanned at 1270 DPI.

Results

Phages of *Desulfovibrio vulgaris* Hildenborough were isolated from a Freeport, Tex. mud sample rinsates using a modification of a standard phage enrichment technique. Even prior to spotting or visualization by EM, the presence of phage in the *Desulfovibrio* enrichment was apparent due to the clearing of the culture and precipitation of iron sulfide. In contrast, the parallel culture of *Desulfovibrio* not exposed to the rinsate remained viable and attached to the inside of the culture tube. The dark black growth of *Desulfovibrio* is characteristic of an SRB cultured in media containing ferrous ammonium sulfate.

A standard assay for phage activity is to spot the phage preparation onto lawns of bacteria and look for clear areas (plaques). When 5 l of E1 or E2 was spotted onto a spread plate lawn of *D. vulgaris* Hildenborough, clearing was observed.

Electron microscopy imaging of E2 revealed the presence of at least two phage types; One is a large, contractile tailed (myophage), with an isometric head size of 125 nm. This head size is characteristic of a phage possessing a genome greater than 150 kb. The other is a smaller myophage with a head size of 45 nm. This is more characteristic of a phage possessing a genome less than 50 kb.

Discussion

In evaluating the use of phage as a natural control agent for corrosion causing SRBs, we have identified natural sources of *Desulfovibrio vulgaris* Hildenborough phage and successfully performed enrichments, killing off the test bacteria. The straightforward isolation of *Desulfovibrio* phage indicates that phages active against members of the SRB are abundant in some environments. At least two novel phages (Dvib1 and Dvib2) capable of lytic growth on *D. vibrio* Hildenborough were isolated in this experiment. Although very different in head diameter, both phages possess typical contractile myophage morphology. Dvib1 has a large non-prolate head, reminiscent of other large isometric myophage such as phiKZ and EL. Dvib2 is a smaller phage, similar in morphology to the Bcep781-like phages. Identified Bcep781-like phages are virulent myophages that plate on *Burkholderia* and *Xanthomonas*. Similar to most bacteria, the isolate of *D. vulgaris* used to propagate these phage are known to be a lysogen. There are at least three prophage present in the genome of *D. vulgaris* Hildenborough: two lambda like phages and two Mu-like phages. Inductions with mitomycin C results in the production of a myophage (which the authors refer to as a "straight tailed phage"), likely to be one of the Mu-like phages, and a siphophage (which the authors refer to as a "bent tailed phage"), likely to be the Lambda like prophage. Both of these can form plaques on the *D. vulgaris* DePue strain but do not form plaques on Hildenborough. Neither Dvib1 or Dvib2 are similar in morphology to these phage. While Dvib2 is a small myophage, the tail to head ratio is clearly different from the previously described temperate phages as Dvib2 tail is shorter compared to the head size. Genomic analysis of Dvib1 and Dvib2 is required to know how these phages are related to other phages. However, given the immense genetic diversity of phage it is very likely that neither phage will be similar at a genomic level to phages currently in the public database.

In an additional test bulk foaming samples were obtained from Willis, Tex. and College Station, Tex. wastewater treatment facilities. Both filamentous *Gordonia* species and phage (s) to destroy them were isolated from these samples in a manner similar to that described in detail above.

In the foregoing specification, the invention has been described with reference to specific embodiments thereof. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

The invention claimed is:

1. A method for reducing bio-corrosion in an industrial water system comprising;

identifying a target bacteria strain in a water system;

locating and enriching a phage virulent for said bacteria strain, and subjecting said water system to an effective amount of said phage to effect a reduction of bio-corrosion of iron containing metal.

2. The method of claim 1 wherein the water system is selected from a group consisting of industrial cooling water, sewage and drinking water, paper making water, swimming pool water, fire extinguisher system water and all forms of industrial process water in any pipe, tank, open pit, pond or channel.

3. The method of claim 1 wherein the effective amount of phage is delivered through a medium that coats at least a portion of the water system.

4. The method of claim 1 wherein the phage(s) are injected into a water system in small discrete amounts that maintain an initial high concentration of phage(s) in the vicinity of the injection.

5. The method of claim 4 wherein the concentration of phage(s) are at least $1\times10^5$ cfu/ml.

6. The method of claim 1 wherein the phage is delivered in a multi-panel consisting of at least two phages virulent for each of two target bacteria stains.

7. The process of claim 6 wherein the multi-panel comprises phage(s) in a concentration of at least $1\times10^7$ cfu/ml.

8. The method of claim 6 wherein the multi-panel consisting of at least two phages virulent for each of the two target bacteria stains comprises bacteriophage virulent for sulfur reducing bacteria and for iron oxidizing bacteria.

9. The method of claim 1 wherein at least one of the virulent phage(s) are isolated from a source in which the virulent phage(s) coexist with its corresponding target bacteria.

10. The method of claim 1 wherein enriched phage is concentrated and freeze dried before being injected into the water system.

11. A process for the remediation of bacterial corrosion of iron containing metals in industrial water systems comprising:

identifying target bacteria in a water system; culturing at least one dominate target bacteria strain;

identifying virulent phage for the target bacteria strain(s);

isolating and enriching phage samples for testing; in-situ testing of the identified virulent phage strains;

preparing suitable quantity of identified phage to treat the target water system, and subjecting the target water source to an effective amount of the identified phage to effect a reduction of iron metal corroding bacteria strains.

12. The process of claim 11 wherein identifying the virulent phage is accomplished by identifying the bacteria strain and empirically applying a phage sample until a kill of the bacteria is obtained.

13. The process of claim 11 wherein identifying the virulent phage is accomplished by empirically finding a matching killer phage from separately collected or stored phage samples.

14. The process of claim 11 wherein the water system is subjected to an effective amount of phage(s) by injecting virulent phage(s) in small discrete amounts that maintain an initial high concentration of phage(s) in the vicinity of the injection.

15. The process of claim 11 wherein the concentration of phage(s) to which the water system is at least $1\times10^5$ cfu/ml.

16. The method of claim 15 wherein the phage is delivered in a multi-panel consisting of at least two phages virulent for each of two target bacteria stains.

17. The process of claim 16 wherein the multi-panel comprises phage(s) in a concentration of at least $1\times10^7$ cfu/ml.

18. The process of claim 11 wherein the effectiveness of the virulent phage first applied is monitored and when loss of effectiveness is determined identifying additional virulent phage to be added to the water source to effect a reduction of bacteria.

* * * * *